US008227209B2

(12) United States Patent
Kiga et al.

(10) Patent No.: US 8,227,209 B2
(45) Date of Patent: Jul. 24, 2012

(54) PROCESS FOR PRODUCING FUNCTIONAL NON-NATURALLY OCCURRING PROTEINS, AND METHOD FOR SITE-SPECIFIC MODIFICATION AND IMMOBILIZATION OF THE PROTEINS

(75) Inventors: Daisuke Kiga, Yokohama (JP); Masahiko Uchiyama, Yokohama (JP)

(73) Assignees: Tokyo Institute of Technology, Tokyo (JP); Celagix Research Ltd., Kanagawa (JP)

( * ) Notice: Subject to any disclaimer, the term of this patent is extended or adjusted under 35 U.S.C. 154(b) by 674 days.

(21) Appl. No.: 12/073,233

(22) Filed: Mar. 3, 2008

(65) Prior Publication Data

US 2009/0011459 A1 Jan. 8, 2009

(30) Foreign Application Priority Data

Mar. 6, 2007 (JP) .................................. 2007-055739

(51) Int. Cl.
*C12N 15/00* (2006.01)
*C12N 15/11* (2006.01)
(52) U.S. Cl. ..................................... 435/69.1; 536/23.1
(58) Field of Classification Search .................. None
See application file for complete search history.

(56) References Cited

U.S. PATENT DOCUMENTS

| 2003/0022230 A1* | 1/2003 | Yanagawa et al. ............... 435/6 |
| 2005/0084856 A1 | 4/2005 | Kiga et al. |

FOREIGN PATENT DOCUMENTS

| JP | 2004-261160 A | 9/2004 |
| WO | WO 03/014354 A1 | 2/2003 |

OTHER PUBLICATIONS

Yamamoto, Yoko et al., "Site-specific PEGylation of a lysine-deficient TNF-α with full bioactivity", Nature Biotechnology, vol. 21, May 2003, pp. 546-552.
Wang, Lei et al., "Addition of the keto functional group to the genetic code of *Escherichia coli*", PNAS, vol. 100, No. 1, Jan. 7, 2003, pp. 56-61.
Miyamoto-Sato, Etsuko et al., "Highly stable and efficient mRNA templates for mRNA-protein fusions and C-terminally labeled proteins", Nucleic Acids Research, vol. 31, No. 15 e78, 2003, pp. 1-9.

Takai, Kazuyuki, et al., "In Vitro Codon-Reading Specificities of Unmodified tRNA Molecules with Different Anticodons on the Sequence Background of *Escherichia coli* tRNA", Biochemical and Biophysical Research Communications, vol. 257, 1999, pp. 662-667.
Nureki, Osamu, et al., "Molecular Recognition of the Identity-determinant Set of Isoleucine Transfer RNA from *Escherichia coli*", J. Mol. Biol., vol. 236, 1994, pp. 710-724.
Nemoto, Naoto, et al., "In vitro virus: Bonding of mRNA bearing puromycin at the 3'-terminal end to the C-terminal end of its encoded protein on the ribosome in vitro", Federation of European Biochemical Societies Letters, vol. 414, 1997, pp. 405-408.
Roberts, Richard, et al., "RNA-peptide fusions for the in vitro selection of peptides and proteins", Proc. Natl. Acad. Sci., vol. 94, Nov. 1997, pp. 12297-12302.
Leung, David et al., "A Method for Random Mutagenesis of a Defined DNA Segment Using a Modified Polymerase Chain Reaction", Journal of Methods in Cell and Molecular Biology, vol. 1, No. 1, Aug. 1989, pp. 11-15.
Stemmer, Willem, "DNA shuffling by random fragmentation and reassembly: In vitro recombination for molecular evolution", Proc. Natl. Acad. Sci., vol. 91, Oct. 1994, pp. 10747-10751.
Flanders, Kathleen Corey, et al., "Semisynthetic Derivatives of Glucagon: (Des-His[1]) N$^\epsilon$-acetimidoglucagon and N$^\alpha$-Biotinyl-N-acetimidoglucagon", Biochemistry, vol. 21, 1982, pp. 4244-4251.
Zhang, Lili, et al., "Calpain Inhibitor I Increases β-Amyloid Peptide Production by Inhibiting the Degradation of the Substrate of γ-Secretase", The Journal of Biological Chemistry, vol. 274, No. 13, 1999, pp. 8966-8972.
Curtis, Sherill, et al., "Demonstration of Sulfhydryl and Disulfide Groups by a Fluorescent Maleimide Procedure", Histochemistry, vol. 68, 1980, pp. 23-28.
Bayer, Edward, et al., "3-(N-Maleimido-propionyl) Biocytin: A Versitile Thiol-Specific Biotinylating Reagent", Analytical Biochemistry, vol. 149, 1985, pp. 529-536.
Giegé, Richard, et al., "Universal rules and idiosyncratic features in tRNA identity", Nucleic Acids Research, vol. 26, No. 22, 1998, pp. 5017-5035.
Kigawa, Takanori, et al., "Preparation of *Escherichia coli* cell extract for highly productive cell-free protein expression", Journal of Structural and Functional Genomics, vol. 5, 2004, pp. 63-68.

* cited by examiner

*Primary Examiner* — Michele K Joike
(74) *Attorney, Agent, or Firm* — Foley & Lardner LLP

(57) ABSTRACT

There is provided a process for industrial production of non-naturally occurring proteins composed of less than 20 amino acids, wherein the proteins retain their original functions while being capable of site-specific modification or immobilization, or having new functions not found in nature in addition to the original functions of the proteins. Specifically there are provided a process for producing a functional non-naturally occurring protein having a specific amino acid type(s) replaced with a natural amino acid(s) other than the amino acid type(s).

6 Claims, 7 Drawing Sheets

| Marker | 1 | 2 | 3 | 4 | 5 | 6 |
|---|---|---|---|---|---|---|
| Alanine tRNA mutant | 0 | 0 | 1 | 0 | 1 | 4 |
| Inhibitor (5 μM) | − | − | − | + | + | + |
| Lys | + | − | − | − | − | − |

SEQUENCE LISTING

```
<160> NUMBER OF SEQ ID NOS: 29

<210> SEQ ID NO 1
<211> LENGTH: 66
<212> TYPE: DNA
<213> ORGANISM: Artificial Sequence
<220> FEATURE:
<223> OTHER INFORMATION: TGTplus

<400> SEQUENCE: 1
gcagcaagct taatacgact cactataggg gctatagctc agctgggaga gcgcctgctt     60
tgtacg                                                                66

<210> SEQ ID NO 2
<211> LENGTH: 72
<212> TYPE: DNA
<213> ORGANISM: Artificial Sequence
<220> FEATURE:
<223> OTHER INFORMATION: TGT_minus

<400> SEQUENCE: 2
```

```
gtcgggatcc tggtggagct atgcgggatc gaaccgcaga cctcctgcgt acaaagcagg    60
cgctctccca gc                                                       72

<210> SEQ ID NO 3
<211> LENGTH: 23
<212> TYPE: DNA
<213> ORGANISM: Artificial Sequence
<220> FEATURE:
<223> OTHER INFORMATION: alaPCRplus

<400> SEQUENCE: 3
gcagcaagct taatacgact cac                                           23

<210> SEQ ID NO 4
<211> LENGTH: 27
<212> TYPE: DNA
<213> ORGANISM: Artificial Sequence
<220> FEATURE:
<223> OTHER INFORMATION: alaPCRminus

<400> SEQUENCE: 4
gtcgggatcc tggtggagct atgcggg                                       27

<210> SEQ ID NO 5
<211> LENGTH: 25
<212> TYPE: DNA
<213> ORGANISM: Artificial Sequence
<220> FEATURE:
<223> OTHER INFORMATION: ala_JUSTminus

<400> SEQUENCE: 5
tggtggagct atgcgggatc gaacc                                         25

<210> SEQ ID NO 6
<211> LENGTH: 66
<212> TYPE: DNA
<213> ORGANISM: Artificial Sequence
<220> FEATURE:
<223> OTHER INFORMATION: GGTplus

<400> SEQUENCE: 6
gcagcaagct taatacgact cactataggg gctatagctc agctgggaga gcgcctgctt    60
ggtacg                                                              66

<210> SEQ ID NO 7
<211> LENGTH: 72
<212> TYPE: DNA
<213> ORGANISM: Artificial Sequence
<220> FEATURE:
<223> OTHER INFORMATION: GGT_minus

<400> SEQUENCE: 7
gtcgggatcc tggtggagct atgcgggatc gaaccgcaga cctcctgcgt accaagcagg    60
cgctctccca gc                                                       72

<210> SEQ ID NO 8
<211> LENGTH: 76
<212> TYPE: RNA
<213> ORGANISM: Artificial Sequence
<220> FEATURE:
<223> OTHER INFORMATION: tRNA Ala (UGU)

<400> SEQUENCE: 8
ggggcuauag cucagcuggg agagcgccug cuuuguacgc aggaggucug cgguucgauc    60
```
ccgcauagcu ccacca                                                76

<210> SEQ ID NO 9
<211> LENGTH: 76
<212> TYPE: RNA
<213> ORGANISM: Artificial Sequence
<220> FEATURE:
<223> OTHER INFORMATION: tRNA Ala (GGU)

<400> SEQUENCE: 9
ggggcuauag cucagcuggg agagcgccug cuugguacgc aggaggucug cgguucgauc    60
ccgcauagcu ccacca                                                76

<210> SEQ ID NO 10
<211> LENGTH: 561
<212> TYPE: DNA
<213> ORGANISM: Artificial Sequence
<220> FEATURE:
<223> OTHER INFORMATION: Ras Protein

<400> SEQUENCE: 10
atgaccgaat acaaactggt tgtagttggc gctggtggtg taggcaaaag cgcgctgacc    60
attcagttga tccagaacca cttcgtagat gagtacgacc cgactattga agactcttac   120
cgtaagcagg ttgttatcga cggtgagacc tgtttgctgg acatccttga taccgcaggc   180
caagaagaat actctgctat gcgtgatcag tatatgcgta ccggcgaagg cttcctgtgc   240
gttttcgcta tcaacaacac caaatctttt gaagacatcc atcaataccg tgaacagatc   300
aaacgtgtta agactctga tgacgttccg atggttctgg ttggtaacaa atgcgacttg   360
gcagcgcgta ctgttgaatc tcgtcaggct caggatctgg ctcgttctta cggaattccg   420
tacatcgaaa cctctgctaa aactcgtcaa ggcgttgaag acgctttcta caccttggtt   480
cgtgaaatcc gtcagcacaa gctgcgtaag cttggatccc tggtgccacg cggtagtcac   540
caccaccacc accactaata a                                             561

<210> SEQ ID NO 11
<211> LENGTH: 39
<212> TYPE: DNA
<213> ORGANISM: Artificial Sequence
<220> FEATURE:
<223> OTHER INFORMATION: GCA_F

<400> SEQUENCE: 11
tcagctggga gagcgcctgc ttgcaacgca ggaggtctg                          39

<210> SEQ ID NO 12
<211> LENGTH: 31
<212> TYPE: DNA
<213> ORGANISM: Artificial Sequence
<220> FEATURE:
<223> OTHER INFORMATION: Mut_R

<400> SEQUENCE: 12
gcaggcgctc tcccagctga gctatagccc c                                  31

<210> SEQ ID NO 13
<211> LENGTH: 39
<212> TYPE: DNA
<213> ORGANISM: Artificial Sequence
<220> FEATURE:
<223> OTHER INFORMATION: TTT_F

<400> SEQUENCE: 13
tcagctggga gagcgcctgc cttttaagca ggaggtctg                                    39

<210> SEQ ID NO 14
<211> LENGTH: 76
<212> TYPE: RNA
<213> ORGANISM: Artificial Sequence
<220> FEATURE:
<223> OTHER INFORMATION: tRNA Ala (GCA)

<400> SEQUENCE: 14
ggggcuauag cucagcuggg agagcgccug cuugcaacgc aggaggucug cgguucgauc    60
ccgcauagcu ccacca                                                    76

<210> SEQ ID NO 15
<211> LENGTH: 76
<212> TYPE: RNA
<213> ORGANISM: Artificial Sequence
<220> FEATURE:
<223> OTHER INFORMATION: tRNA Ala (UUU)

<400> SEQUENCE: 15
ggggcuauag cucagcuggg agagcgccug ccuuuuaagc aggaggucug cgguucgauc    60
ccgcauagcu ccacca                                                    76

<210> SEQ ID NO 16
<211> LENGTH: 561
<212> TYPE: DNA
<213> ORGANISM: Artificial Sequence
<220> FEATURE:
<223> OTHER INFORMATION: StAvM4

<400> SEQUENCE: 16
atggctagca tgactggtgg acagcaaatg ggtaccgaat tccatatgga cccgtccaag    60
gactccaaag ctcaggtttc tgcagccgaa gctggtatca ctggcacctg gtataaccaa   120
ctggggtcga cttcattgt gaccgctggt gcggacggag ctctgactgg cacctacgaa    180
tctgcggttg gtaacgcaga atcccgctac accctgactg gccgttatga ctctgcacct   240
gccaccgatg gctctggtac cgctctgggc tggcgtgtgg cttggaaaaa caactatcgt   300
aatgcgcaca cgccactac gtggtctggc caatacgttg gcggtgctga ggctcgtatc   360
aacactcagt ggaccttaac atccggcact accgaagcga atgcatggaa atcgacacta   420
cgtggtcatg acacctttac caaagttaag ccttctgctg ctagcattga tgctgccaag   480
aaagcaggcg taaacaacgg taaccctcta gacgctgttc agcaacgcgg taatagccac   540
caccaccacc accactaata a                                             561

<210> SEQ ID NO 17
<211> LENGTH: 561
<212> TYPE: DNA
<213> ORGANISM: Artificial Sequence
<220> FEATURE:
<223> OTHER INFORMATION: StAvM4_KallA

<400> SEQUENCE: 17
atggctagca tgactggtgg acagcaaatg ggtaccgaat tccatatgga cccgtccgct    60
gactccgcag ctcaggtttc tgcagccgaa gctggtatca ctggcacctg gtataaccaa   120
ctggggtcga cttcattgt gaccgctggt gcggacggag ctctgactgg cacctacgaa    180
tctgcggttg gtaacgcaga atcccgctac accctgactg gccgttatga ctctgcacct   240
gccaccgatg gctctggtac cgctctgggc tggcgtgtgg cttgggcaaa caactatcgt   300

```
aatgcgcaca gcgccactac gtggtctggc caatacgttg gcggtgctga ggctcgtatc    360
aacactcagt ggaccttaac atccggcact accgaagcga atgcatgggc atcgacacta    420
cgtggtcatg acacctttac cgcagttgct ccttctgctg ctagcattga tgctgccgct    480
gcagcaggcg taaacaacgg taaccctcta gacgctgttc agcaacgcgg taatagccac    540
caccaccacc accactaata a                                              561
```

```
<210> SEQ ID NO 18
<211> LENGTH: 99
<212> TYPE: DNA
<213> ORGANISM: Artificial Sequence
<220> FEATURE:
<223> OTHER INFORMATION: pSER_F

<400> SEQUENCE: 18
ttgtaaaacg acggccagtg ccaagcttaa tacgactcac tataggaagt gtggccgagc    60
ggttgaaggc accggtcttg aaaaccggcg acccgaaag                           99
```

```
<210> SEQ ID NO 19
<211> LENGTH: 99
<212> TYPE: DNA
<213> ORGANISM: Artificial Sequence
<220> FEATURE:
<223> OTHER INFORMATION: pSER_R

<400> SEQUENCE: 19
agctatgacc atgattacga attcgagctc ggtacccgcc ttcccggcgg aagcgcagag    60
attcgaactc tggaaccctt tcgggtcgcc ggttttcaa                           99
```

```
<210> SEQ ID NO 20
<211> LENGTH: 25
<212> TYPE: DNA
<213> ORGANISM: Artificial Sequence
<220> FEATURE:
<223> OTHER INFORMATION: MT

<400> SEQUENCE: 20
acgacgttgt aaaacgacgg ccagt                                          25
```

```
<210> SEQ ID NO 21
<211> LENGTH: 25
<212> TYPE: DNA
<213> ORGANISM: Artificial Sequence
<220> FEATURE:
<223> OTHER INFORMATION: REV

<400> SEQUENCE: 21
caggaaacag ctatgaccat gatta                                          25
```

```
<210> SEQ ID NO 22
<211> LENGTH: 38
<212> TYPE: DNA
<213> ORGANISM: Artificial Sequence
<220> FEATURE:
<223> OTHER INFORMATION: GCA1_SF

<400> SEQUENCE: 22
gttgaaggca ccggtctgca aaaccggcga cccgaaag                            38
```

```
<210> SEQ ID NO 23
<211> LENGTH: 32
<212> TYPE: DNA
<213> ORGANISM: Artificial Sequence
```

```
<220> FEATURE:
<223> OTHER INFORMATION: Mut_SR

<400> SEQUENCE: 23
accggtgcct caaccgctc ggccacactt cc                                    32

<210> SEQ ID NO 24
<211> LENGTH: 38
<212> TYPE: DNA
<213> ORGANISM: Artificial Sequence
<220> FEATURE:
<223> OTHER INFORMATION: GCA2_SF

<400> SEQUENCE: 24
gttgaaggca ccggtttgca acaccggcga cccgaaag                             38

<210> SEQ ID NO 25
<211> LENGTH: 21
<212> TYPE: DNA
<213> ORGANISM: Artificial Sequence
<220> FEATURE:
<223> OTHER INFORMATION: SerJustMinus

<400> SEQUENCE: 25
tggcggaagc gcagagattc g                                               21

<210> SEQ ID NO 26
<211> LENGTH: 88
<212> TYPE: RNA
<213> ORGANISM: Artificial Sequence
<220> FEATURE:
<223> OTHER INFORMATION: tRNA Ser (GCA1)

<400> SEQUENCE: 26
ggaagugugg ccgagcgguu gaaggcaccg gucugcaaaa ccggcgaccc gaaaggguuc     60
cagaguucga aucucugcgc uuccgcca                                        88

<210> SEQ ID NO 27
<211> LENGTH: 88
<212> TYPE: RNA
<213> ORGANISM: Artificial Sequence
<220> FEATURE:
<223> OTHER INFORMATION: tRNA Ser (GCA2)

<400> SEQUENCE: 27
ggaagugugg ccgagcgguu gaaggcaccg guuugcacca ccggcgaccc gaaaggguuc     60
cagaguucga aucucugcgc uuccgcca                                        88

<210> SEQ ID NO 28
<211> LENGTH: 38
<212> TYPE: DNA
<213> ORGANISM: Artificial Sequence
<220> FEATURE:
<223> OTHER INFORMATION: TTT_SF

<400> SEQUENCE: 28
gttgaaggca ccggtctttt aaaccggcga cccgaaag                             38

<210> SEQ ID NO 29
<211> LENGTH: 88
<212> TYPE: RNA
<213> ORGANISM: Artificial Sequence
<220> FEATURE:
<223> OTHER INFORMATION: tRNA Ser (UUU)
```

```
<400> SEQUENCE: 29
ggaagugugg ccgagcgguu gaaggcaccg gucuuuuaaa ccggcgaccc gaaaggguuc     60
cagaguucga aucucugcgc uuccgcca                                       88
```

PROCESS FOR PRODUCING FUNCTIONAL NON-NATURALLY OCCURRING PROTEINS, AND METHOD FOR SITE-SPECIFIC MODIFICATION AND IMMOBILIZATION OF THE PROTEINS

FIELD OF THE INVENTION

The present invention relates to a process for industrial production of a functional non-naturally occurring protein composed of less than 20 amino acids, that is capable of site-specific modification or immobilization or further has an antioxidant property. In particular, the invention relates to a process for industrial production of a functional non-naturally occurring protein having alanine or serine incorporated in a site-specific manner to replace specific amino acids, the process making use of an in vitro evolutionary molecular engineering technique with in vitro virus that includes using an alanine tRNA mutant or serine tRNA mutant.

BACKGROUND OF THE INVENTION

Naturally occurring proteins acquire increased activity through the repeated evolutionary cycle of selection, mutation and amplification of genes. In the organism, most proteins are modified for variation of their functional groups and therefore exhibit considerable functional variation. The advent of evolutionary molecular engineering of proteins has led to artificial creation of proteins or of genetic DNA encoding therefor that form the basis of bioreactions, in the laboratory, for industrial use. The technology has made possible the emergence of enzymes and proteins exhibiting new activity not found in nature, or proteins with significantly different structures from natural proteins, which are expected to have a variety of applications in the fields of medicine and engineering. Evolutionary molecular engineering involves the selection of molecules having desired activity from among a random polymer pool of block units of amino acids or nucleotides making up proteins or the genes encoding them.

However, it has been desired to increase protein functional group variation, and to develop additional protein immobilization and protein stabilization techniques suitable for bioprocessing, in order to achieve further advances in the field. The key to such advances is protein modification technology. For example, modification of a protein used in treatments for hepatitis, interferon, with polyethylene glycol (PEG) has successfully increased in vivo stability and lengthened elimination half-life in blood, even when the modification is nonspecific. Modification techniques are also very similar to protein immobilization techniques, that are important for bioprocessing and for increased functionality of cell culture dishes. In other words, the difference between the techniques is simply whether the substance added to the protein by modification is smaller than a given size, or whether it is a support.

Methods for site-specific modification of proteins that have become known in recent years include a method of designing a mutant having all of the lysine residues of a protein replaced or a mutant having all but one of the cysteine residues replaced, in order to limit the modification site to a single location (for example, see Nature Biotechnology, 2003, vol. 21, pp. 546-552). However, large-scale amino acid-substitution that replaces a given type(s) of amino acid at most of all sites, has been associated with the drawback of reduced protein activity. Also, major effort has been required to explore mutants that compensate for the reduced activity.

In a reported system for development of the method described above, a phage display is used to select a protein that has no lysine residues but still retains activity, from among an initial library wherein all the lysine codons at six locations are randomized. However, because only a very few clones had all of the lysines replaced, it is expected that the efficiency of obtaining active clones with lysines replaced will be even lower for other proteins in general. Also, it is assumed that unintended mutations during the course of preparing the library resulted in lysine codons even at sites that did not code for lysine in the original protein. In fact, the activities of the clones obtained in the aforementioned report were only moderate.

There are also known methods wherein a protein synthesis system containing an added aaRS (aminoacyl tRNA synthase) mutant is used to introduce amino acids other than the usual 20 (non-naturally occurring amino acids) during protein synthesis (for example, see Japanese Unexamined Patent Publication (Kokai) No. 2004-261160, International Patent Publication No. WO 03/014354, and PNAS Jan. 7, 2003, vol. 100, No. 1, pp. 56-61). In the former cited document, production of a protein with introduction of highly reactive non-naturally occurring amino acids containing ketone groups or the like is followed by reaction of the functional groups for modification (PNAS Jan. 7, 2003, vol. 100, No. 1, pp. 56-61). In the latter cited documents, non-naturally occurring amino acids with the intended modifications are introduced into the protein directly on the ribosome (Japanese Unexamined Patent Publication (Kokai) No. 2004-261160, and International Patent Publication No. WO 03/014354). These methods have the advantage of allowing site-specific modification without reduction in activity, and without the use of evolutionary molecular engineering techniques.

However, since it is rarely possible to obtain the desired properties simply by site-specific mutagenesis using rational design of protein mutants, and most proteins exhibit reduced activity as a result, evolutionary molecular engineering must be applied for practical results. For mass production, such methods must employ protein synthesis systems with yet additional special features. Other major problems are that the fidelity of such protein synthesis systems is low, and the proteins obtained as industrial products are not homogeneous. One of the methods also requires preparation of a specialized aaRS mutant for each type of non-naturally occurring amino acid. Preparation of such mutants is not only difficult currently, but the non-naturally occurring amino acids are also limited in their physical size in order to be acceptable for the various aspects of protein synthesis.

SUMMARY OF THE INVENTION

It is therefore not easy, with the prior inventions for protein synthesis methods, to accomplish inexpensive and large scale production (especially on the milligram level) of proteins with new activities not found in nature by introduction of a chemical structure significantly different from natural proteins. In contrast, although protein mutants without one or more types of 20 naturally occurring amino acids can be produced by conventional protein synthesis methods and have useful property for modification, immobilization, or anti-oxidization property, such mutants usually have decreased activity. Although evolutionary molecular engineering technique usually allows isolation of mutants with high or new activity, this technique can not be applied for isolation of protein mutants without one or more types of 20 naturally occurring amino acids, because mutagenesis necessary for preparation of a second generation library can be followed by reappearance of the type(s) of amino acids which should be excluded from the mutants.

Therefore, the present invention relates to a process for industrial production of non-naturally occurring proteins, wherein a specific amino acid type(s) are replaced with natural amino acids other than the specific amino acid type(s), and the proteins retain their original functions while being capable of site-specific modification or immobilization, or having new functions not found in nature in addition to the original functions of the proteins.

As a result of much diligent research in light of the current state of the art, the present inventor has found that by creating an alanine tRNA mutant and/or serine tRNA mutant for a specific amino acid type(s) to be excluded from the protein-composing amino acids, and applying a known in vitro virus (mRNA display) method to a cell-free protein synthesis system containing the tRNA mutant(s) and natural amino acids other than the specific amino acid type(s), it is possible to produce a non-naturally occurring protein with specific activity, without resulting in reappearance of the amino acid type(s) excluded once from the initial library by molecular evolution.

In addition, it was found that by synthesis ("gene resynthesis") of a polynucleotide composed of a nucleotide sequence encoding for an amino acid sequence based on amino acid sequence information for a protein produced by the process of the invention, and by use of the polynucleotide in a known protein synthesis system (a protein synthesis system containing naturally-occurring amino acids), it is possible to inexpensively and mass produce the functional non-naturally occurring protein.

Further, it was found that when a non-site-specific method, even if specific for an amino acid type(s), is applied from among ordinary protein modification methods and immobilization methods to the functional non-naturally occurring protein obtained by the production process of the invention, it is possible to accomplish site-specific modification and immobilization.

Specifically, the invention provides the following:

(1) A process for producing a functional non-naturally occurring protein having a specific amino acid type(s) replaced with a natural amino acid(s) other than the amino acid type(s), the process comprising:

a) matching a nucleic acid portion having a nucleotide sequence reflecting the genotype with a protein portion that is the translation product of the nucleic acid portion;

b) selecting the matched molecule obtained in step a);

c) introducing mutation into the nucleic acid portion of the matched molecule obtained in step b);

d) amplifying the nucleic acid portion obtained in step c);

e) providing the nucleic acid portion obtained in step d) to step a), to match the nucleic acid portion with a protein portion that is the translation product of the nucleic acid portion; and f) selecting the matched molecule obtained in step e), to produce a functional non-naturally occurring protein.

(2) The process according to (1), which further comprises providing the nucleic acid portion obtained in step d) to step a), to repeat steps a)-d).

(3) The process according to (1), characterized in that the nucleic acid portion is mRNA, and in step a), a spacer is ligated to the 3'-end of the mRNA after which a nucleoside or nucleoside analog capable of covalently linking to amino acids is ligated to the 3'-end of the ligated structure to obtain an mRNA ligated structure, and then the mRNA ligated structure is added to a cell-free protein synthesis system comprising a suppressor tRNA corresponding to the specific amino acid type(s) and natural amino acids other than the specific amino acid type(s), for protein synthesis, whereby the translation product of the mRNA ligated structure is ligated with the mRNA ligated structure.

(4) The process according to (1), wherein the specific amino acid is threonine, lysine and/or cysteine.

(5) The process according to (3), wherein the suppressor tRNA is an alanine tRNA mutant and/or serine tRNA mutant.

(6). The process according to (3), wherein the nucleoside or nucleoside analog is puromycin.

(7) The process according to (1), characterized by preparing a polynucleotide comprising a nucleotide sequence which encodes the amino acid sequence of a protein produced by the steps a) and b), and by subjecting the polynucleotide to a protein synthesis system containing 20 amino acids.

(8) A method for site-specific modification of a functional non-naturally occurring protein, characterized in that a protein produced by the process according to (3) is modified by a protein modification reagent for a specific amino acid type(s).

(9) The method according to (8), characterized in that a protein produced by the process according to (3) is site-specific modified at its N-terminus, by a protein modification reagent for a specific amino acid type(s).

(10) The method according to (8), characterized in that the lysine codons are reintroduced into at any locations of a protein produced by the process according to (3), and the site(s) is modified by a protein modification reagent for a lysine residue.

(11) The method according to (8), characterized in that the cysteine codons are reintroduced into at any locations of a protein produced by the process according to (3), and the site(s) is modified by a protein modification reagent for a cysteine residue.

(12) A method for site-specific immobilization of a functional non-naturally occurring protein, characterized in that a specific amino acid residue of a protein produced by the process according to (3), is bound to an immobilizing carrier.

BEST MODE FOR CARRYING OUT THE INVENTION

Figure 1:
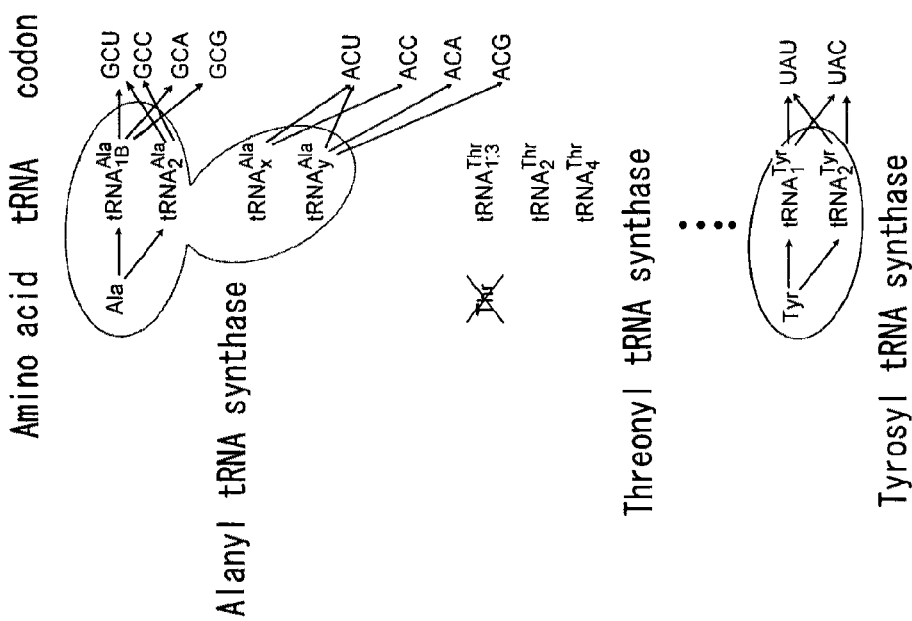
FIG. 1 shows an "artificial genetic code table without threonine", wherein alanine is assigned to the threonine codons, in place of threonine, as an example of an artificial genetic code table used for the process of the invention.

It must be noted that, as used in this specification and the intended claims, the singular form "a", "an" or "the" may include plural referents unless the context clearly dictates otherwise.

Since the process for producing a functional non-naturally occurring protein according to the invention can avoid reappearance of amino acids that have been excluded from the original library, due to alternation of generations, it has thereby become possible for the first time to promote a cycle of evolutionary molecular engineering aimed at reducing an amino acid type(s), thus actually achieving an effect of restricting the amino acid type(s).

Furthermore, resynthesis of the gene for the produced protein allows industrial production of a functional non-naturally occurring protein according to the invention, even using a known protein synthesis system.

Amino acids in natural protein synthesis systems each have a special aminoacyl tRNA synthase (hereinafter referred to as "aaRS") for each amino acid, which was bound to the corresponding tRNA by the enzyme. Each tRNA-bound amino acid is used for protein synthesis in correspondence with its tRNA anticodon, regardless of whether it is bound to its cognate tRNA. It is a characteristic that the aaRS strictly recognizes only the corresponding tRNA among all of the tRNAs (which have L-shaped spatial configurations), and strictly recognizes only the corresponding amino acid from among all of amino acid types having similar chemical structures. If a matching error occurs with aaRS, therefore, proper protein synthesis will not occur. The essence of the genetic code table is a system with a perfectly optimized matching relationship.

Polymerization of amino acids on the ribosome to form proteins requires bonding of the amino acids to tRNAs by aaRS. Therefore, by excluding from the protein synthesis system a specific type(s) of amino acid, or the aaRS or tRNA corresponding to the amino acid, it is possible to "exclude" a specific type(s) of amino acid from the protein.

Exclusion of an amino acid type(s) can be easily accomplished using cell-free protein synthesis reaction, since virtually all of the cell-derived small molecules in the cell extract used in cell-free protein synthesis reaction are removed by dialysis after disruption and centrifugation of the cells. Since the amino acids used for synthesis are added separately, it is possible to exclude a given type(s) of amino acid by not adding it during the step. The term "exclude" with reference to a specific amino acid type(s), as used herein, means that the specific amino acid type(s) is "replaced" with another natural amino acid.

The amino acid-related factors may be removed by, for example, a method in which tRNA(s) for a specific amino acid type(s) is removed with an immobilized probe DNA or the like, or a method in which aaRS(s) for the amino acid(s) is removed by an immobilized antibody. It is known that in a cell-free protein synthesis system, reconstitution can be accomplished by separately adjusting the individual factors, but another method may also be employed, in which the reaction solution used does not include specific factors mixed, in construction of the reconstituted cell-free protein synthesis system. A inhibitor specific for an aminoacyl tRNA synthase(s) may also be used.

However, simple exclusion of a factor(s) causes protein synthesis to terminate at the codons corresponding to the excluded amino acid(s), making it impossible to obtain the full-length protein. The use of "suppressor tRNA" is a feature of the process of the invention. A naturally occurring nonsense suppressor tRNA has an anticodon corresponding to a stop codon (which normally does not have a corresponding tRNA and thus terminates protein synthesis). Even with a mutation in the anticodon, the amino acid still binds to the tRNA by the aaRS so that an amino acid is inserted into the peptide chain at the stop codon, allowing nonsense suppression. FIG. 1 shows an example of using "suppressor tRNA" that inserts alanine in place of threonine for the codons for threonine which is an amino acid excluded from the genetic code table.

The process of the invention is characterized by using a "suppressor tRNA" to construct a "matched molecule" for the nucleic acid portion (genotype) and the protein portion as the translation product of the nucleic acid portion (phenotype) in a cell-free protein synthesis system, selecting the matched molecule by an in vitro selection method based on specific activity, amplifying a selected in vitro virus gene portion by PCR, and if necessary, repeating the procedures of construction of the matched molecule, mutagenesis and amplification.

A "matched molecule" may be a viral type that forms a complex of the genotype and phenotype, a ribozyme type that mounts the genotype and phenotype on the same molecule, or a cellular type that places the genotype and phenotype in the same enclosure (Tanpakushitsu Kakusan Kouso, Vol. 48 No. 11 (2003)). The process of the invention is preferably an "in vitro virus method" wherein the mRNA and protein are covalently linked.

As other virus evolutionary molecular engineering methods for integrating genotypes and phenotypes there may be mentioned phage display (Smith, G. P., Science 228, 1315-1317 (1985); Scott, J. K., Science 249, 386-390 (1990)), polysome display (Mattheakis, L. C. et al., Proc. Natl. Acad. Sci. USA 91, 9022-9026 (1994)), coded tagged library (Brenner, S et al., Proc. Natl. Acad. Sci. USA 89, 5381-5383 (1992)) and Cellstat (Husimi, Y. et al., Rev. Sci. Instrum. 53, 517-522 (1982)).

The process of the invention will now be described based on an in vitro virus method, and the details of the procedures of matched molecule construction, selection, mutagenesis and amplification may be found in International Patent Publication No. WO 98/16636.

(A) Matching

The matching may be accomplished by ligating a spacer to the 3'-end of mRNA, subsequently ligating a nucleoside or nucleoside analog capable of covalently bonding with a nascent peptide on a ribosome at the 3'-end of the ligated structure to obtain an mRNA ligated structure, and then adding the mRNA ligated structure to a cell-free protein synthesis system comprising a suppressor tRNA(s) and natural amino acids other than the specific amino acid type(s) which is excluded, for protein synthesis, and ligating the translation product of the mRNA ligated structure with the mRNA ligated structure by covalent bonding.

According to this matching method, when the codons for the specific excluded amino acid type(s) are encountered in protein synthesis, the suppressor tRNA enters the A site of the ribosome. The nucleoside or nucleoside analog at the 3'-end of the suppressor tRNA binds with the protein by the action of peptidyl transferase.

The initial library of the mRNA used for the invention contains mRNA of the wild-type nucleotide sequence, mRNA mutants having a nucleotide sequence wherein all of the codons for the amino acid type(s) to be excluded are replaced with codons for amino acid type(s) with similar chemical properties, and mRNA mutants having a nucleotide sequence wherein the codons for the amino acid type(s) to be excluded are randomized. The second generation mRNA library may include, in addition to the mRNA or mRNA mutant of the initial library, an mRNA mutant obtained via a step of matching, selection, mutagenesis and amplification using mRNA of the initial library.

The "spacer" may be any one that is a high molecular substance with a length of 100 Å or greater and even more preferably about 100-1000 Å. Specifically, there may be mentioned macromolecules such as natural or synthetic single-stranded DNA or RNA; DNA/DNA double-strands, and polysaccharides, polyethylene glycol and the like. Polyethylene glycol preferably has a molecular weight of about 2,000-30,000.

As examples of the "nucleoside or nucleoside analog" capable of covalently binding with amino acids there may be mentioned puromycin and 3'-N-aminoacylpuromycin aminonucleosides (PANS-amino acid) (for example, PANS-Gly for glycine, PANS-Val for valine or PANS-Ala for alanine), which form amide bonds at the 3'-end of nucleic acids. There may also be used 3'-N-aminoacyl adenosine amino nucleosides (AANS-amino acid) (for example, AANS-Gly for glycine, AANS-Val for valine or AANS-Ala for alanine), having amide bonds formed as a result of dehydrating condensation of amino acid carboxyl groups with 3'-aminoadenosine amino groups, and ester-bound products of nucleosides and amino acids. Puromycin is more preferred among these.

The mRNA ligated structure of the invention may be, for example, mRNA (5' untranslated region-start codon-protein coding region)-3' untranslated region-DNA spacer-puromycin. The ligated structure may be obtained by covalent bonding of mRNA having the eight nucleotides AAAAAAAA as the 3' untranslated region, with "phosphate group-d(CC)-(Spacer18)$_8$-dCC-puromycin" ("molecule α") (Spacer18: —(CH$_2$)$_2$—O—[(CH$_2$)$_2$O]$_8$—PO$_3$—), prior to the translation reaction. The covalent bond may be formed using RNA ligase (Nucleic Acids Research vol. 31, e78, 2003) or by an ordinary organic chemical reaction. Bonding between molecule α and mRNA may be accomplished, specifically, by using T4 RNA ligase (Takara Co.) and adding polyethylene glycol 2000 to the accompanying buffering solution at a final concentration of 120 μM. The reaction temperature is about 15° C., and the reaction time is approximately 4 hours.

The ligation product of the mRNA and molecule α is applied to the cell-free protein synthesis system comprising the suppressor tRNA(s) and natural amino acids other than the specific type(s) of amino acid which is excluded. Then, MgCl$_2$ and KCl at a final concentration of 50 mM, 500 mM, respectively, are added to the reaction mixture obtained, and the reaction mixture is allowed to stand at about 10° C. for about 30 minutes to form an mRNA-DNA spacer-puromycin-protein complex.

Examples of a suppressor tRNA(s) to be used for the invention can include an "alanine tRNA mutant," which has the anticodon for the specific type of amino acid to be excluded and in which alanine is bound instead of the above amino acid by the aaRS (Giege R. et al., Nucleic Acids Research 1998, vol. 26, No. 22, pp. 5017-5035). In addition to the alanine tRNA mutant, a "serine tRNA mutant" may be also used, which has the anticodon for the specific type of amino acid to be exclude and in which serine is bound instead of the above amino acid by the aaRS (Takai K. et al., Biochemical and Biophysical Research Communications 257, 662-667 (1999)). Since the aaRS for these tRNA mutants do not recognize anticodon, they can bind alanine or serine even to tRNA having mutations introduced into the anticodon. One or more than one amino acid type may be excluded, but preferably no more than ten and more preferably no more than five are excluded from the viewpoint of expressing activity and forming a three dimensional structure.

For example, when threonine is excluded from the protein-forming amino acids, first in order to assign alanine instead of threonine to the four codons encoding threonine, a set of alanine tRNA mutants having either the anticodon "UGU" or the anticodon "GGU", capable of pairing with the four codons (ACU, ACC, ACA, ACG), was prepared by T7 in vitro transcription.

An alanine tRNA mutant having the anticodon "UGU" can be prepared in the following manner. First, a TGT-containing DNA fragment is provided for PCR, and after cleaving the obtained PCR product with HindIII and BamHI, it is inserted into the HindIII-BamHI site of vector pUC18 to create vector pALA (TGT), E. coli is used to clone the vector, and then PCR reaction is performed to prepare template DNA for transcription of the alanine tRNA mutant. The obtained PCR product contains the promoter sequence of T7 RNA polymerase and the tRNA sequence downstream from it, and serves as template for in vitro transcription. The transcription template may then be used for transcription and purification according to a method described in the literature (Nureki O. et al., J. Mol. Biol. 236, 710-724, 1994), to obtain an alanine tRNA mutant.

By then adding the set of alanine tRNA mutants to a cell-free protein synthesis reaction solution containing no threonine, "suppression" occurs whereby alanine is inserted into the polypeptide chain at the threonine codons, and a full-length translation product is obtained.

Exclusion of the specific amino acid type(s) from a protein can be also used to eliminate instability of proteins due to chemical modification on the amino acid level. For example, oxidation of the sulfur-containing amino acid cysteine results in formation of undesired disulfide bonds, potentially inactivating the protein. Oxygen atoms are added to methionine by oxidation, and the resulting steric hindrance can lower protein activity. In order to impart a protein with an oxidization resistant property, it is necessary to exclude the oxidizable amino acids such as cysteine and methionine from the protein. However, the following problems are associated with excluding cysteine and methionine.

With exclusion of an amino acid type(s) having less than four codons such as cysteine, lysine or asparagine, misreading between the codons can occur. Specifically, recognition of codon/anticodon pairs may take place between the 3rd letter of the codon and the 1st letter of the anticodon in a manner other than Watson-Crick recognition of adenine-uracil and guanine-cytosine. In order to avoid cross reaction between different amino acid tRNAs that have the same 1st and 2nd letters of the codon, it is common in wild-type tRNA for there to be modification of the 1st letter of the anticodon that pairs with the 3rd letter of the codon. Since the anticodon "GCA" in tRNA pairing with the codon "UGU" or "UGC" for cysteine is not modified in E. coli endogenous tRNA, modification is probably not necessary for a tRNA mutant having alanine or serine inserted in place of cysteine, for the purpose of the invention. Similarly, modification is also probably unnecessary for a tRNA mutant having the anticodon "CUU" that pairs with the codon "AAG" for lysine.

On the other hand, in the absence of modification of "U" as the 1st letter of the anticodon in a tRNA mutant having the anticodon "UUU" that pairs with the codon "AAA", the tRNA might pair with the asparagine codon "AAU" or "AAC", though at low efficiency. As a result, a very small amount of serine or alanine might be erroneously inserted instead of the original asparagine at the polypeptide site corresponding to the asparagine codon.

Such failure to properly read the codon by the tRNA mutant with the anticodon "UUU" can be avoided by the means such as:

(1) adding the absolute minimum amount of tRNA mutant necessary;

(2) increasing the amount of asparagine tRNA (competition between this asparagine tRNA and the tRNA mutant eliminates translation errors due to the relatively small amount of tRNA mutant used);

(3) introducing modifications that maintain accuracy of codon/anticodon recognition, into the tRNA mutant to be prepared in the T7 in vitro transcription (genes mnmA and iscS that have anticodon modifying enzyme activity have been identified, and in vitro modification systems using these gene products have already been reported, and so these enzymes are prepared);

(4) additionally assigning asparagine to the codon "AAG" or "AAA" (when asparagine is also assigned to the codon "AAG" or "AAA", no alanine tRNA mutant is used, and instead, an asparagine tRNA mutant in which an anticodon is replaced, is used. Replacement of the asparagine tRNA anticodon can reduce recognition by the enzyme that binds asparagine and tRNA, but this can be countered by modifying the enzyme as well so that it recognizes the tRNA mutant. It is thereby possible to properly insert only asparagine for the asparagine codons.); and (5) adding a set of alanine tRNA mutants or that of serine tRNA mutants capable of matching with all AAN codons, after excluding not only lysine but also asparagine from the protein synthesis system.

By applying the same method for other amino acid types as well, it is possible to avoid the problem caused by codon/anticodon ambiguity.

Similarly, replacing a specific amino acid type(s) with alanine or serine in the genetic code table can exclude any type(s) of amino acids from the protein translation system. However, since the polypeptide obtained thereby has a number of replacements from the wild-type sequence, the polypeptide will in almost all cases have lower activity than the natural form. In order to obtain a protein with specific functions retained or improved, repeating of the steps of selection, mutagenesis and amplification is required.

(b) Selection

The term "selection" as used herein means a step of evaluating the function (bioactivity) of the protein portion composing the in vitro virus and selecting the in vitro virus based on the desired bioactivity. Such methods are known and may be found, for example, in Nemoto N. et al., FEBS letters 1997, vol. 414, pp. 405-408; and Roberts R W. et al., PNAS, 1997, vol. 94, pp. 12297-12302.

The functions used for selection according to the invention include, for example, the original activity of the protein before the replacements of a type(s) of amino acids at all sites of the protein, as well as oxidization resistant property, protein-binding activity, stability and enzyme activity newly acquired by the replacements of the mutant protein. For selection of interferon mutants with specific binding ability, for example, an interferon receptor, antibody or the like may be first immobilized on a known support such as beads, and reacted with a matched molecule comprising an interferon polypeptide mutant and its mRNA, to allow selection of interferon mutant with high binding activity.

In the subsequent steps of c) mutagenesis and d) amplification, mutations are introduced into the selected in vitro virus mRNA and amplification is carried out by PCR or the like. Specifically, the mutations can be introduced after synthesis of cDNA by reverse transcriptase, or the mRNA may be amplified with introduction of mutations. Mutagenesis may be easily accomplished using the already established method of error-prone PCR (Leung, D. W. et al., J. Methods Cell Mol. Biol., 1, 11-15, 1989) or sexual PCR (Stemmer, W. P. C., Proc. Natl. Acad. Sci. USA 91, 10747-10751, 1994).

The mutated and amplified in vitro virus mRNA may be used for steps of: e) providing the nucleic acid portion obtained in step d) to step a), to match the nucleic acid portion with the translation product thereof; and f) selecting the matched molecule with desired bioactivity. If necessary, steps a)-d) may be repeated for modification and creation of functional non-naturally occurring proteins. More importantly, use of the alanine tRNA mutant(s) or serine tRNA mutant(s) can prevent reappearance of the amino acid type(s) that should be excluded from the initial library in the obtained protein.

However, since the aforementioned process for producing a functional non-naturally occurring protein relies on a cell-free system employing a special translation system, the protein synthesis efficiency is not very high. Therefore, in order to obtain a large amount of non-naturally occurring protein, it is preferred to employ an ordinary protein synthesis system. The term "ordinary protein synthesis system" refers to protein synthesis system which can use all 20 amino acids, which may be either cellular or cell-free.

Since the protein synthesis system of the invention uses codons for an excluded amino acid(s) to specify an amino acid other than that amino acid(s), the gene encoding the protein obtained by the aforementioned evolution cycle can contain the codons for the excluded amino acid(s). Thus, the excluded amino acid(s) may reappear if the gene is applied in an ordinary protein synthesis system. Therefore, an artificial gene that allows creation of the "amino acid sequence of the obtained functional non-naturally occurring protein" according to the genetic code table is resynthesized utilizing a synthetic polynucleotide. Total synthesis of genes is now a routine laboratory technique, and can be economically accomplished. For example, when the evolution cycle is carried out using a special genetic code table where alanine is assigned to the lysine codons, since the obtained gene may include the codons "AAA" and "AAG", a gene with these codons replaced by the alanine codons ("GCU", "GCC", "GCA" or "GCG") is "resynthesized".

The resynthesized artificial gene may be applied to an ordinary protein synthesis system containing no suppressor tRNA to allow inexpensive and convenient mass production (for example, on the milligram level or gram level) of a functional non-naturally occurring protein retaining the amino acid sequence obtained in the evolution cycle.

Therefore, the process of the invention makes it possible to create a protein having a specific function. Furthermore, the created protein can be modified or immobilized in a site specific manner as described below using conventional reagents.

The modification may be performed using "a protein modification reagent for a specific amino acid type(s)."

As used herein, the term "a protein modification reagent for a specific amino acid type(s)" refers to a reagent modifying only the specified amino acid residue(s), among 20 amino acid residues listed in the normal genetic code table. One protein molecule may usually have a specific amino acid type(s), such as lysine, at several locations of an amino acid sequence of the protein. Therefore, the protein would be modified at several lysine residues by the protein modification reagent. If one protein molecule has a specific amino acid type(s) at only one position of an amino acid sequence of the protein, the protein would be site-specifically modified at the specific amino acid residue by the protein modification reagent. The protein modification reagent includes NHS (N-hydroxysuccinimide)-activated modifiers, maleimide-activated modifiers or the like. NHS-activated modifiers are described in detail in Flanders K C et al., Biochemistry, 1982, vol. 21, pp. 4244-4251 and Zhang L. et al., Journal of Biological Chemistry, 1999, vol. 274, pp. 8966-8972; and maleimide-activated modifiers are described in Curtis S K and Cowden R R., Histochem., 1980, vol. 68, pp. 23-28 and Analytical Biochemistry, 1985, vol. 149, pp. 529-536. It should be noted that "a protein modification reagent for lysine" targets not only an amino group at a lysine side chain but also that at the N-terminus of a protein. For example, if the N-terminus of the lysine-free non-naturally occurring protein is a free amino group, such a site can be used as the specific modification site using NHS-activated modifier which is known as inexpensive amino group-modifying reagent. When the N-terminus is formylated, acetylated or the like, the lysine codon(s) may be reintroduced at specific location(s) which may be the modification or immobilization site(s). When the N-terminus is not protected, the N-terminal fragment may be cleaved by some means. Site-specific modification at any location(s) other than the terminus of the non-naturally occurring protein can be accomplished using reintroduction of codon(s) for cysteine.

By a similar procedure, it is possible to achieve immobilization via a specific amino acid residue of the non-naturally occurring protein, onto an immobilizing carrier. The immobilizing carrier may be provided with a support composed of a solid that is insoluble in water or organic solvents, as well as a reactive group bound on the support. Examples of supports there can include those commonly used for immobilization of proteins, such as latex particles, agarose beads, Sepharose beads, magnetic beads, microtiter plates, nitrocellulose membranes, nylon membranes and the like. An immobilizing carrier having the non-naturally occurring protein immobilized thereon may be used for affinity chromatography, a protein chip, a bioreactor or the like. Such carrier may be also used for implant materials or artificial materials for regenerative medicine, onto which extracellular matrix components such as collagen, proteoglycan, fibronectin, elastin and hyaluronic acid, or cellular adhesion molecules such as the cadherin family, immunoglobulin superfamily, integrin family, selectin family, link protein family or sialomucin family are immobilized.

EXAMPLES

The present invention will now be described in greater detail by examples, with the understanding that the invention is not limited to these examples.

Example 1

Preparation of Alanine tRNA Mutant

```
(1) SEQ ID NO: 1: TGTplus
GCAGCAAGCTTAATACGACTCACTATAGGGGCTATAGCTCAGCTGGGAGA

GCGCCTGCTTTGTACG (2) SEQ ID NO: 2: TGT_minus
GTCGGGATCCTGGTGGAGCTATGCGGGATCGAACCGCAGACCTCCTGCGT

ACAAAGCAGGCGCTCTCCCAGC (3) SEQ ID NO: 3: alaPCRplus
GCAGCAAGCTTAATACGACTCAC (4) SEQ ID NO: 4: alaPCRminus
GTCGGGATCCTGGTGGAGCTATGCGGG (5) SEQ ID NO: 5: ala_JUSTminus
TGGTGGAGCTATGCGGGATCGAACC (6) SEQ ID NO: 6: GGTplus
GCAGCAAGCTTAATACGACTCACTATAGGGGCTATAGCTCAGCTGGGAGA

GCGCCTGCTTGGTACG (7) SEQ ID NO: 7: GGT_minus
GTCGGGATCCTGGTGGAGCTATGCGGGATCGAACCGCAGACCTCCTGCGT

ACCAAGCAGGCGCTCTCCCAGC
```

Template DNA for transcription of an alanine tRNA mutant with the anticodon site replaced by TGT was prepared in the following manner.

First, 50 μL of PCR reaction mixture containing 5 pmol each of DNA (1) and DNA (2) (the rest of the composition was according to the instruction manual for Takara Pyrobest DNA polymerase) was prepared, and 5 cycles of PCR were performed. Next, 40 pmol each of DNA (3) and DNA (4) were added and 15 more cycles of PCR were performed. The obtained PCR product was cleaved with HindIII and BamHI, and then incorporated at the HindIII-BamHI site of vector pUC18 (TOYOBO) to prepare vector pALA (TGT). After confirming the sequence of the vector cloned in E. coli, DNA (3) and DNA (5) were used for PCR using KOD DNA polymerase. The reaction conditions were according to the package insert for the enzyme.

The obtained PCR product contains the promoter sequence of T7 RNA polymerase and the tRNA sequence downstream from it, and serves as template for in vitro transcription. DNA (6) and DNA (7) were also used instead of DNA (1) and DNA (2) to prepare template DNA that transcribes an alanine tRNA mutant having the anticodon site replaced by GGT.

The DNA of these transcription templates were used for transcription reaction and purification by a method described in the literature (J. Mol. Biol. 236, 710-724, 1994) to obtain an alanine tRNA mutant. The sequences were as follows, where the underlines indicate anticodons.

```
SEQ ID NO: 8: tRNA Ala (UGU)
GGGGCUAUAGCUCAGCUGGGAGAGCGCCUGCUUUGUACGCAGGAGGUCUG

CGGUUCGAUCCCGCAUAGCUCCACCA

SEQ ID NO: 9: tRNA Ala (GGU)
GGGGCUAUAGCUCAGCUGGGAGAGCGCCUGCUUGGUACGCAGGAGGUCUG

CGGUUCGAUCCCGCAUAGCUCCACCA
```

The four threonine codons (ACU, ACC, ACA, ACG) can be recognized with these two tRNAs.

Example 2

Threonine-Excluded Cell-Free Translation Reaction Using Alanine tRNA Mutant

Cell-free protein synthesis reaction was conducted according to Journal of Structural and Functional Genomics, 2004; 5(1-2):63-8. The composition of the reaction mixture was as follows: 55 mM Hepes-KOH (pH 7.5), 1.7 mM DTT, 1.2 mM ATP (pH 7.0), 0.8 mM each of CTP (pH 7.0), GTP (pH 7.0)

and UTP (pH 7.0), 80 mM CP, 250 µg/ml creatine kinase, 4.0% polyethylene glycol 8000, 0.64 mM 3',5'-cyclic AMP, 68 µM L(−)-5-formyl-5,6,7,8-tetrahydrofolic acid, 175 µg/ml E. coli total tRNA, 210 mM potassium glutamate, 27.5 mM ammonium acetate, 10.7 mM magnesium acetate, 1.0 mM each of amino acids, $^{14}$C-leucine, 6.7 µg/ml translation template plasmid, 93 µg/ml T7 RNA polymerase and 30% (w/v) S30 extract. The cell extract S30 used was prepared by purchasing a commercially available kit and dialysing against a buffering solution (10 mM Tris acetate (pH 8.2), 14 mM Mg(OAc)$_2$, 60 mM KOAc, 1 mM DTT). A comparative test was conducted using all 20 amino acids, and using the 19 amino acids other than threonine. Two different alanine tRNA mutants were added in 0, 1, 2 and 4 µM concentrations.

Figure 2:
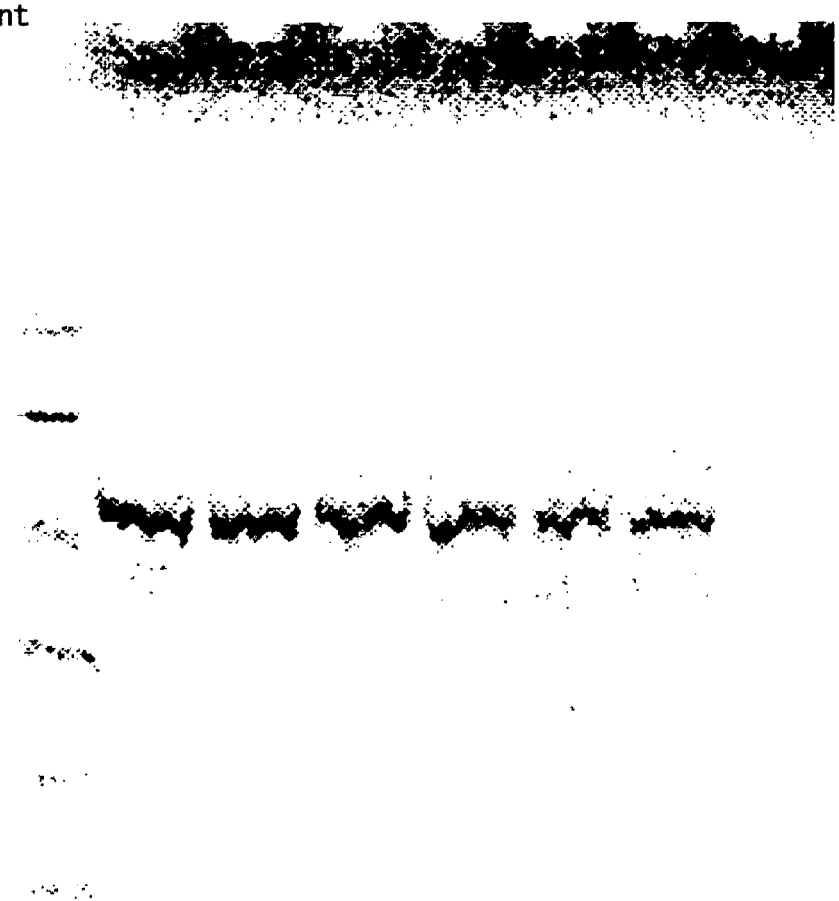
FIG. 2 is a photograph of SDS-PAGE showing the results of a cell-free translation reaction without threonine.

The template used was the Ras protein coding sequence (SEQ ID NO: 10). After 60 minutes of translation reaction (translation is presumed to result in a protein with a molecular weight of approximately 21,000), the reaction product was analyzed using 4-12% NuPAGE Bis-Tris gel (Invitrogen). After drying the gel, it was analyzed using an image analyzer (Fuji Film Corp.). The results are shown in FIG. 2. All of lanes 1-3 are positive controls containing all 20 amino acids.

As shown in FIG. 2, bands were detected at approximately the predicted molecular weight. It was demonstrated that the copresence of the alanine tRNA mutants yielded a full-length translation product even without threonine in the reaction mixture (lanes 4-6). On the other hand, no full-length translation product was obtained when neither threonine nor alanine tRNA mutant were present (lane 7).

It was therefore presumed that, in lanes 4-6, alanine had been introduced into the protein, in place of threonine codons.

Example 3

Preparation of Alanine tRNA Mutants for Lysine and Cysteine Codons

Template DNA transcribing an alanine tRNA mutant having the anticodon site replaced by either GCA or TTT was prepared in the following manner.

The two oligo DNAs GCA_F (SEQ ID NO: 11) and Mut_R (SEQ ID NO: 12) were used against the pALA (TGT) prepared in Example 1 to construct vector pALA (GCA), using a QuikChange Site-Directed Mutagenesis Kit (STRATAGENE). Similarly, TTT_F (SEQ ID NO: 13) and Mut_R were used to construct pALA (TTT).

```
SEQ ID NO: 11: GCA_F
TCAGCTGGGAGAGCGCCTGCTTGCAACGCAGGAGGTCTG

SEQ ID NO: 12: Mut_R
GCAGGCGCTCTCCCAGCTGAGCTATAGCCCC

SEQ ID NO: 13: TTT_F
TCAGCTGGGAGAGCGCCTGCCTTTTAAGCAGGAGGTCTG
```

An alanine tRNA mutant was then prepared in the same manner as Example 1. The sequences were as follows, where the underlines indicate anticodons.

```
SEQ ID NO: 14: tRNA Ala (GCA)
GGGGCUAUAGCUCAGCUGGGAGAGCGCCUGCUUGCAACGCAGGAGGUCUG

CGGUUCGAUCCCGCAUAGCUCCACCA

SEQ ID NO: 15: tRNA Ala (UUU)
GGGGCUAUAGCUCAGCUGGGAGAGCGCCUGCCUUUUAAGCAGGAGGUCUG

CGGUUCGAUCCCGCAUAGCUCCACCA
```

The tRNAs can recognize the two cysteine codons (UGU, UGC) or the two lysine codons (AAA, AAG), respectively.

Example 4

Lysine-Excluded Cell-Free Translation Reaction Using Alanine tRNA Mutant

Figure 3:
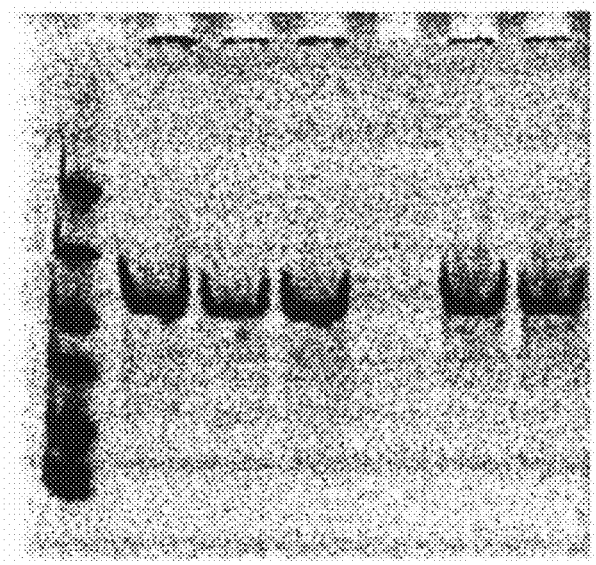
FIG. 3 is a photograph of SDS-PAGE showing the results of a cell-free translation reaction in Example 4, with alanine introduced in place of lysine for the lysine codons.

Cell-free protein synthesis was carried out in the same manner as Example 2. A comparative test was conducted using all 20 amino acids and using the 19 amino acids other than lysine, and the alanine tRNA mutant: tRNA Ala (UUU) was added in a concentration range of 0 µM, 1 µM and 4 µM. In addition, 5 µM 5'-O—[N-(L-lysyl)sulfamoyl]-adenosine was also added. As template for protein synthesis, mRNA having the coding sequence for monomeric streptavidin (SEQ ID NO: 16) was used. The results are shown in FIG. 3. Lane 1 is a positive control containing all 20 amino acids.

As shown in FIG. 3, bands were detected at approximately the predicted molecular weight. Even when lysine was not added to the reaction mixture, a trace amount of protein was synthesized due to the small amount of lysine that had not been removed by dialysis (lane 2), but this production was eliminated by addition of a lysyl tRNA synthase inhibitor (lane 4). It was also shown that addition of the alanine tRNA mutant: tRNA Ala (UUU) yielded the full-length translation product (lanes 5-6).

It is therefore presumed that in lanes 5-6, alanine had been introduced in place of lysine for the lysine codons in the protein.

Purification:

Introduction of alanine in place of lysine for the lysine codons in the protein, was confirmed by mass spectrometry. Monomeric streptavidin was used as the gene for translation. As a control experiment against lysine exclusion, a cell-free protein synthesis system without lysine exclusion was used, with both an His-tagged monomeric streptavidin gene and the same gene having all of the lysine codons replaced with alanine codons.

Reaction was also conducted in the same manner (but without using RI), and 90 µL of the cell-free protein synthesis reaction mixture was collected in a 1.6 mL tube. After adding 900 µL phosphate buffer (pH 7.8) (8.8 M urea, 300 mM NaCl) to the collected sample, it was stirred at 37° C. for 1 hour with a vortex mixer. The sample treated in the vortex mixer was taken in cell-free protein synthesis reaction mixture aliquots of 40 µL-45 µL/bead (i) (450 µL of sample treated in vortex mixer).

There were then combined 40 µL of Co Beads preconditioned with phosphate buffer (pH 7.8) (8 M urea, 300 mM NaCl) (50% slurry) and an equivalent of 45 µL of cell-free protein synthesis reaction sample taken in (i) (450 µL of sample treated in the vortex mixer) (ii). After further adding 500 µL of phosphate buffer (pH 7.8) (8 M urea, 300 mM NaCl) to (ii), the mixture was treated with a rotator at room temperature for 1 hour, and the Co Beads and the protein prepared by cell-free protein synthesis were combined (iii). This was followed by centrifugation of (iii) at 5000 rpm for 1 minute, and the supernatant was discarded leaving the beads in the tube. After adding 500 µL phosphate buffer (pH 7.8) (8 M urea, 300 mM NaCl) to each tube and stirring, it was subjected to a centrifugation procedure at 5000 rpm, 1 minute and the supernatant was discarded (procedure 1). Procedure 1 was repeated two more times. After then adding 20 µL phosphate buffer (pH 6.0) (8 M urea, 300 mM NaCl), the mixture was allowed to stand at room temperature for 5 minutes and subjected to a centrifugation procedure at 9000 rpm, 1 minute, and the supernatant was recovered (procedure 2). Procedure 2 was repeated one more time. After then adding 20 μL phosphate buffer (pH 5.3) (8 M urea, 300 mM NaCl), the mixture was allowed to stand at room temperature for 5 minutes and subjected to a centrifugation procedure at 9000 rpm, 1 minute, and the supernatant was recovered (procedure 3). Procedure 3 was repeated one more time. After then adding 20 μL phosphate buffer (pH 4.0) (8 M urea, 300 mM NaCl), the mixture was allowed to stand at room temperature for 5 minutes and subjected to a centrifugation procedure at 9000 rpm, 1 minute, and the supernatant was recovered (procedure 4). Procedure 4 was repeated one more time. The samples recovered from procedures 2-4 were subjected to SDS-PAGE, the SDS-PAGE gel was stained with CBB, and samples free of other contaminated proteins were recovered as samples for MALDI-TOF/MS (Matrix Assisted Laser Desorption-Ionization Time-Of-Flight Mass Spectrometry).

Figure 4:
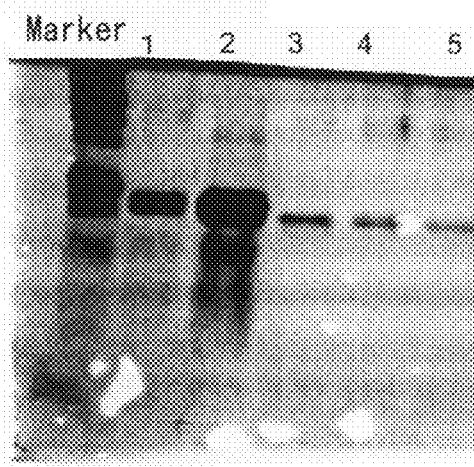
FIG. 4 is a photograph of SDS-PAGE showing the results of purifying StAvM4 produced by cell-free translation reaction in Example 4.

FIG. 4 shows the results of purification. Lanes 1 and 2 are control proteins produced using *E. coli*, lane 1 being monomeric streptavidin (StAvM4) and lane 2 being a mutant (StAvM4_KallA) having all of 8 lysine residues of StAvM4 replaced with alanine. The mRNA encoding StAvM4_KallA is listed as SEQ ID NO: 17. Lanes 3-5 are proteins produced by cell-free protein synthesis reaction. Lane 3 and 4 are control experiments. A cell-free protein synthesis system without lysine exclusion was used for translation reaction from a monomeric streptavidin gene (lane 3) and the same gene having all of the lysine codons replaced with alanine codons (lane 4). Lane 5 shows a translation product for lysine-excluded translation reaction from the monomeric streptavidin gene, where alanine is presumed to be introduced for the lysine codon, in place of lysine.

Figure 5:
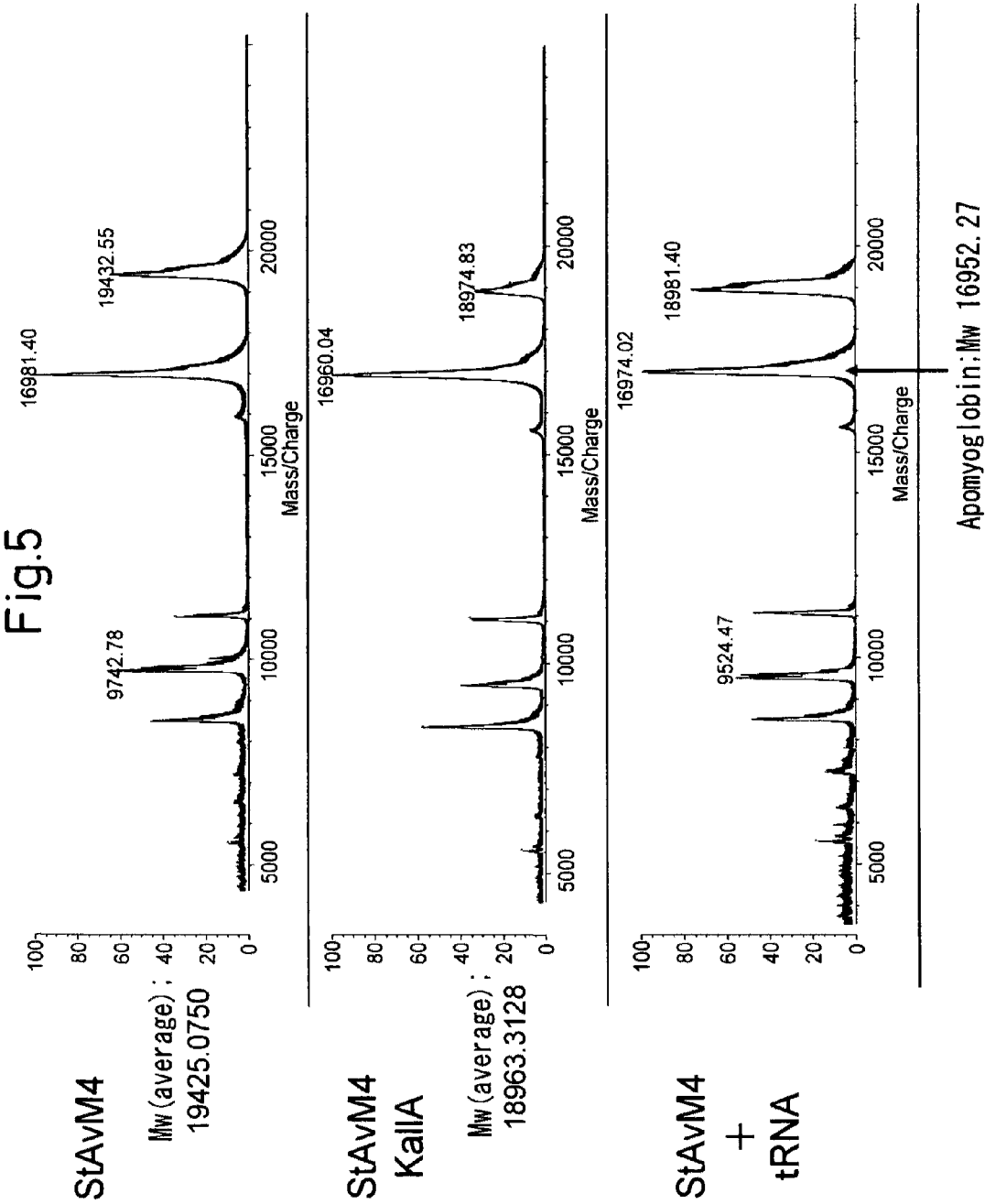
FIG. 5 shows the results of MALDI-TOF/MS mass spectrometry of a protein produced by the cell-free translation reaction in Example 4, where alanine has been introduced in place of lysine for the lysine codons.

Preparation of MALDI-TOF/MS Sample:

After adding 1 μL of 10 mg/mL sinapic acid (water:acetonitrile=1:1) dropwise onto a plate, it was allowed to stand until dry. After drying, 2.5 μmol of apomyoglobin was overlaid onto the dried sinapic acid and allowed to stand until dry. A 10 μL portion of the purified sample (corresponding to about 200 ng) was loaded to a ZipTip preconditioned in a 2% acetonitrile solution (0.1% TFA). Aspiration/discharge of the sample using the ZipTip was repeated five times and followed by a final discharge. Next, aspiration/discharge of about 10 μL of 2% acetonitrile solution (0.1% TFA) was repeated (procedure 5). Procedure 5 was repeated one more time. Approximately 2 μL of 60% acetonitrile was then aspirated and overlaid onto the plate with the dried sinapic acid and apomyoglobin, and allowed to stand until dry. After drying, 1 μL of 10 mg/mL sinapic acid was overlaid and allowed to stand until dry, and the crystallized sample was measured by a MALDI-TOF/MS apparatus by Shimadzu. The results are shown in FIG. 5. The upper graph in FIG. 5 is the spectrum for StAvM4, the middle one is the spectrum for StAvM4_KallA and the lower one is the spectrum for protein obtained by the process of the invention. Comparing the control results of protein synthesis system using a genetic code table (upper and middle graphs) with the results of protein synthesis system of the invention, shows that alanine is inserted for the lysine codon in place of lysine in this system.

Example 5

Cysteine-Excluded Cell-Free Translation Reaction Using Alanine tRNA Mutant

Figure 6:
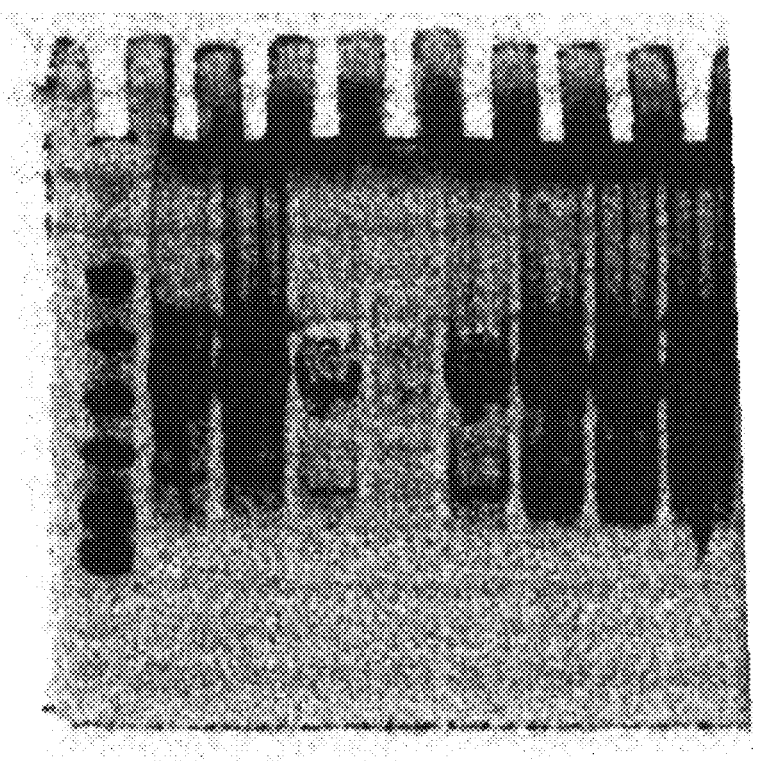
FIG. 6 is a photograph of SDS-PAGE showing the results of the cell-free translation reaction in Example 5, where alanine has been introduced in place of cysteine for the cysteine codons.

Cell-free protein synthesis was carried out in the same manner as Example 2. However, a comparative test was conducted using all 20 amino acids and using the 19 amino acids other than cysteine, and an alanine tRNA mutant (GCA) was added in 0 μM, 0.03 μM, 0.1 μM, 0.3 μM and 1 μM concentrations. Also, 5'-O—[N-(L-cysteinyl)sulfamoyl]-adenosine was added to 5 μM as a cysteinyl tRNA synthase inhibitor. The results are shown in FIG. 6. Lanes 1 and 2 are positive controls containing all 20 amino acids.

As FIG. 6 clearly shows, bands were detected at approximately the predicted molecular weight. Even when cysteine was not added to the reaction mixture, a trace amount of protein was synthesized due to the small amount of cysteine that had not been removed by dialysis (lane 3), but this production was eliminated by addition of a cysteinyl tRNA synthase inhibitor (lane 4). It was also shown that addition of the alanine tRNA mutant: tRNA Ala (GCA) yielded the full-length translation product (lanes 5-8). It is therefore presumed that in lanes 5-8, alanine had been introduced in place of cysteine for the cysteine codons in the protein.

Example 6

Cysteine-Excluded Cell-Free Translation Reaction Using Serine tRNA Mutant

Plasmid pSER (TGA) encoding serine tRNA was prepared in the same manner as Example 1. However, pSER_F (SEQ ID NO: 18) and pSER_R (SEQ ID NO: 19) were used for the initial 5 cycles of PCR, and MT (SEQ ID NO: 20) and REV (SEQ ID NO: 21) were used for the following 15 cycles of PCR. Also, pUC118 (TOYOBO) was used as the vector for integration and HindIII and EcoRI were used as the restriction enzyme combination.

```
SEQ ID NO: 18: pSER_F
TTGTAAAACGACGGCCAGTGCCAAGCTTAATACGACTCACTATAGGAAGT

GTGGCCGAGCGGTTGAAGGCACCGGTCTTGAAAACCGGCGACCCGAAAG

SEQ ID NO: 19: pSER_R
AGCTATGACCATGATTACGAATTCGAGCTCGGTACCCGCCTTCCCGGCGG

AAGCGCAGAGATTCGAACTCTGGAACCCTTTCGGGTCGCCGGTTTTCAA

SEQ ID NO: 20: MT
ACGACGTTGTAAAACGACGGCCAGT

SEQ ID NO: 21: REV
CAGGAAACAGCTATGACCATGATTA
```

The two oligo DNAs GCA1_SF (SEQ ID NO: 22) and Mut_SR (SEQ ID NO: 23) were used on the earlier prepared pSER (TGA) to prepare vector pSER (GCA 1), using a QuikChange Site-Directed Mutagenesis Kit (Stratagene). Similarly, GCA2_SF (SEQ ID NO: 24) and Mut_SR were used to prepare pSER (GCA 2).

```
SEQ ID NO: 22: GCA1_SF
GTTGAAGGCACCGGTCTGCAAAACCGGCGACCCGAAAG

SEQ ID NO: 23: Mut_SR
ACCGGTGCCTTCAACCGCTCGGCCACACTTCC

SEQ ID NO: 24: GCA2_SF
GTTGAAGGCACCGGTTTGCAACACCGGCGACCCGAAAG
```

Serine RNA mutants were then prepared in the same manner as Example 1. However, MT and SerJustMinus (SEQ ID NO: 25) were used as the PCR primers.

SEQ ID NO: 25: SerJustMinus
TGGCGGAAGCGCAGAGATTCG

The sequences of the prepared serine RNA mutants were as follows, where the underlines indicate anticodons.

SEQ ID NO: 26: tRNA Ser (GCA1)
GGAAGUGUGGCCGAGCGGUUGAAGGCACCGGUCU<u>GCA</u>AAACCGGCGACCC

GAAAGGGUUCCAGAGUUCGAAUCUCUGCGCUUCCGCCA

SEQ ID NO: 27: tRNA Ser (GCA2)
GGAAGUGUGGCCGAGCGGUUGAAGGCACCGGUUU<u>GCA</u>CCACCGGCGACCC

GAAAGGGUUCCAGAGUUCGAAUCUCUGCGCUUCCGCCA

Both of the aforementioned tRNAs can recognize the two cysteine codons (UGU, UGC).

Cell-free protein synthesis reaction was carried out in the same manner as Example 5. However, as tRNA mutants there were used the serine tRNA mutant: tRNA Ser (GCA1) in concentrations of 0 μM, 0.25 μM, 1.0 μM and 2.8 μM, and the serine tRNA mutant: tRNA Ser (GCA2) in concentrations of 0 μM, 0.3 μM, 1.0 μM and 3.4 μM. The results are shown in FIG. 7.

Figure 7:
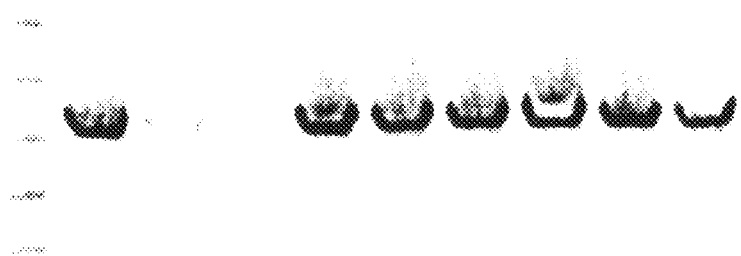
FIG. 7 is a photograph of SDS-PAGE showing the results of the cell-free translation reaction in Example 6, where serine has been introduced in place of cysteine for the cysteine codons.

As shown in FIG. 7, bands were detected at approximately the predicted molecular weight. Even when cysteine was not added to the reaction mixture, a trace amount of protein was synthesized due to the small amount of cysteine that had not been removed by dialysis (lane 2), but this production was eliminated by addition of a cysteinyl tRNA synthase inhibitor (lane 3). It was also shown that addition of the serine tRNA mutants tRNA Ser (GCA1) and tRNA Ser (GCA2) can yield a full-length translation product (lanes 4-6 and 7-9).

It is therefore presumed that in lanes 4-9, serine had been introduced in place of cysteine for the cysteine codons in the protein.

Example 7

Lysine-Excluded Cell-Free Translation Reaction Using Serine tRNA Mutant

Plasmid pSER (TTT) encoding a serine tRNA mutant was prepared in the same manner as Example 6. However, the primers used were TTT_SF (SEQ ID NO: 28) and Mut_SR (SEQ ID NO: 23).

SEQ ID NO: 28: TTT_SF
GTTGAAGGCACCGGTCTTTTAAACCGGCGACCCGAAAG

A serine RNA mutant was then prepared. The sequence of the prepared serine RNA mutant was as follows, where the underlines indicate anticodons.

SEQ ID NO: 29: tRNA Ser (UUU)
GGAAGUGUGGCCGAGCGGUUGAAGGCACCGGUCU<u>UUU</u>AAACCGGCGACCC

GAAAGGGUUCCAGAGUUCGAAUCUCUGCGCUUCCGCCA

This tRNA can recognize the two lysine codons (AAG, AAA).

Figure 8:
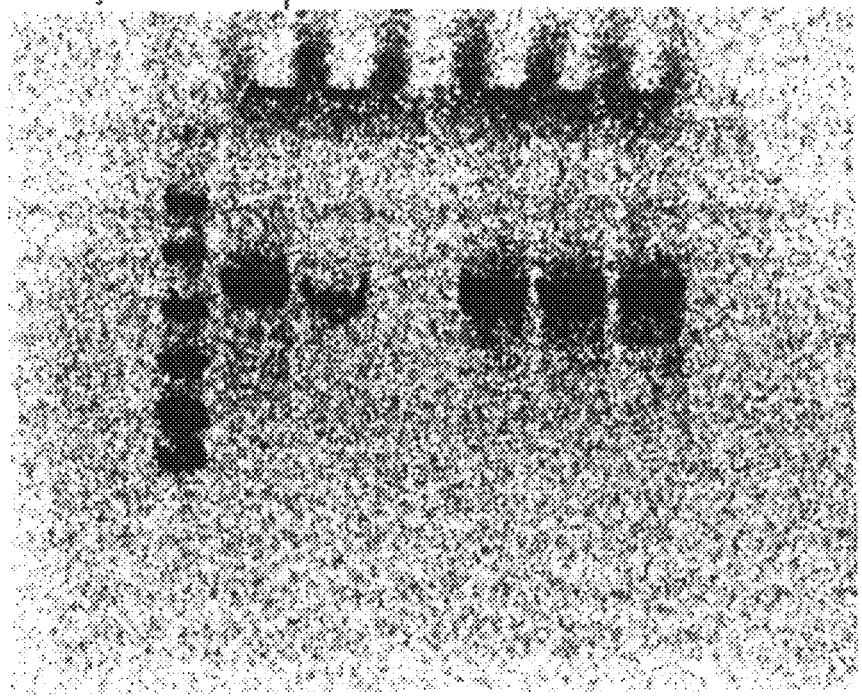
FIG. 8 is a photograph of SDS-PAGE showing the results of the cell-free translation reaction in Example 7, where serine has been introduced in place of lysine for the lysine codons.

Cell-free protein synthesis reaction was carried out in the same manner as Example 4. However, the serine tRNA mutant: tRNA Ser (UUU) was added as a tRNA mutant in concentrations of 0 μM, 0.3 μM, 1.0 μM and 3.0 μM. As template for protein synthesis, the coding sequence for Ras protein (SEQ ID NO: 10) was used. The results are shown in FIG. 8. Lane 1 is a positive control containing all 20 amino acids.

As shown in FIG. 8, bands were detected at approximately the predicted molecular weight. Even when lysine was not added to the reaction mixture, a trace amount of protein was synthesized due to the small amount of lysine that had not been removed by dialysis (lane 2), but this production was eliminated by addition of a lysyl tRNA synthase inhibitor (lane 3). It was also shown that addition of the serine tRNA mutant: tRNA Ser (UUU) could yield a full-length translation product (lanes 4-6). It is therefore presumed that in lanes 4-6, serine had been introduced in place of lysine for the lysine codons in the protein.

---

What is claimed is:

1. A process for producing a functional non-naturally occurring protein having a specific amino acid type(s) replaced with a natural amino acid(s) other than the specific amino acid type(s), the process comprising:
   a) matching a nucleic acid portion having a nucleotide sequence reflecting the genotype with a protein portion that is a product translated from the nucleic acid portion in a cell-free protein synthesis system comprising (i) a suppressor tRNA(s) corresponding to codon(s) for the specific amino acid type(s) to be replaced, thereby inserting into a synthesized protein another amino acid instead of the specific amino acid type(s) to be replaced; (ii) natural amino acids other than the specific amino acid type(s), and (iii) optionally an inhibitor(s) specific for an aminoacyl-tRNA synthetase(s) for the specific amino acid type(s), to obtain a matched molecule containing the nucleic acid portion and the protein portion;
   b) selecting the matched molecule obtained in step a), and if the matched molecule is determined to have a selected activity, then performing step e); otherwise, performing next step c);
   c) introducing a mutation into the nucleic acid portion of the matched molecule obtained in step b);
   d) amplifying the nucleic acid portion obtained in step c), and repeating steps a)-c) utilizing the nucleic acid portion of step d); and
   e) obtaining a functional non-naturally occurring protein having the same amino acid sequence of the protein portion of the matched molecule obtained in step b), by using a protein synthesis system containing naturally occurring amino acids.

2. The process according to claim 1, wherein the nucleic acid portion is mRNA, and in step a), a spacer is ligated to the 3'-end of the mRNA after which a nucleoside or nucleoside analog capable of covalently linking to amino acids is ligated to the 3'-end of the ligated structure to obtain an mRNA ligated structure, and then the mRNA ligated structure is added to the cell-free protein synthesis system for protein synthesis, whereby the translation product of the mRNA ligated structure is ligated with the mRNA ligated structure.

3. The process according to claim 1, wherein the specific amino acid is threonine, lysine and/or cysteine.

4. The process according to claim 2, wherein the suppressor tRNA is an alanine tRNA mutant and/or serine tRNA mutant.

5. The process according to claim 2, wherein the nucleoside or nucleoside analog is puromycin.

6. The process according to claim 1, wherein the protein synthesis in step e) uses a polynucleotide template which has been synthesized so as to encode the same amino acid sequence of the protein portion of the matched molecule obtained in step b).

* * * * *